United States Patent
Dangoisse

(12) 
(10) Patent No.: US 9,504,801 B2
(45) Date of Patent: Nov. 29, 2016

(54) GUIDING CATHETER

(76) Inventor: Vincent Dangoisse, Aiseau-Presles (BE)

(*) Notice: Subject to any disclaimer, the term of this patent is extended or adjusted under 35 U.S.C. 154(b) by 143 days.

(21) Appl. No.: 14/007,915

(22) PCT Filed: Mar. 28, 2012

(86) PCT No.: PCT/EP2012/055507
§ 371 (c)(1),
(2), (4) Date: Dec. 2, 2013

(87) PCT Pub. No.: WO2012/130878
PCT Pub. Date: Oct. 4, 2012

(65) Prior Publication Data
US 2014/0088566 A1    Mar. 27, 2014

Related U.S. Application Data

(60) Provisional application No. 61/469,465, filed on Mar. 30, 2011.

(30) Foreign Application Priority Data

Mar. 30, 2011    (EP) .................................... 11160351

(51) Int. Cl.
A61M 25/00    (2006.01)
A61M 25/06    (2006.01)

(52) U.S. Cl.
CPC .......... *A61M 25/0041* (2013.01); *A61M 25/00* (2013.01); *A61M 25/0021* (2013.01); *A61M 25/0662* (2013.01); *A61M 2025/0042* (2013.01); *A61M 2210/125* (2013.01)

(58) Field of Classification Search
CPC .......... A61M 25/00; A61M 25/0021; A61M 25/0023; A61M 25/0041; A61M 2025/0042; A61M 2210/125
See application file for complete search history.

(56) References Cited

U.S. PATENT DOCUMENTS

| | | | | |
|---|---|---|---|---|
| 5,215,540 A | * | 6/1993 | Anderhub | 604/532 |
| 5,306,263 A | * | 4/1994 | Voda | 604/532 |
| 5,471,986 A | * | 12/1995 | Ishimura et al. | 600/435 |
| 5,876,385 A | * | 3/1999 | Ikari et al. | 604/523 |
| 6,002,955 A | | 12/1999 | Willems et al. | |
| 6,558,368 B1 | | 5/2003 | Voda | |
| 2002/0013547 A1 | | 1/2002 | Paskar | |

FOREIGN PATENT DOCUMENTS

| | | |
|---|---|---|
| EP | 0727237 | 8/1996 |
| EP | 1920795 | 5/2008 |
| WO | 9638196 | 12/1996 |

OTHER PUBLICATIONS

European Patent Office International Search Report dated May 22, 2012, International Application No. PCT/EP2012/055507 (3 pages).

* cited by examiner

*Primary Examiner* — Imani Hayman
*Assistant Examiner* — Nilay Shah
(74) *Attorney, Agent, or Firm* — Koppel Patrick Heybl & Philpott, P.C.

(57) ABSTRACT

Guiding catheter comprising a first end and a second end, and at least three main portions being: a first linear portion connected to the first end, a second curved portion connected to the first linear portion, a third linear portion, connected to the second curved portion, opposite to the first linear portion, and connected to said second end, characterized in that said second curved portion subtends an angle β from 195° to 240° and in that said third linear portion is provided to engage an active distal tip as fourth portion.

19 Claims, 6 Drawing Sheets

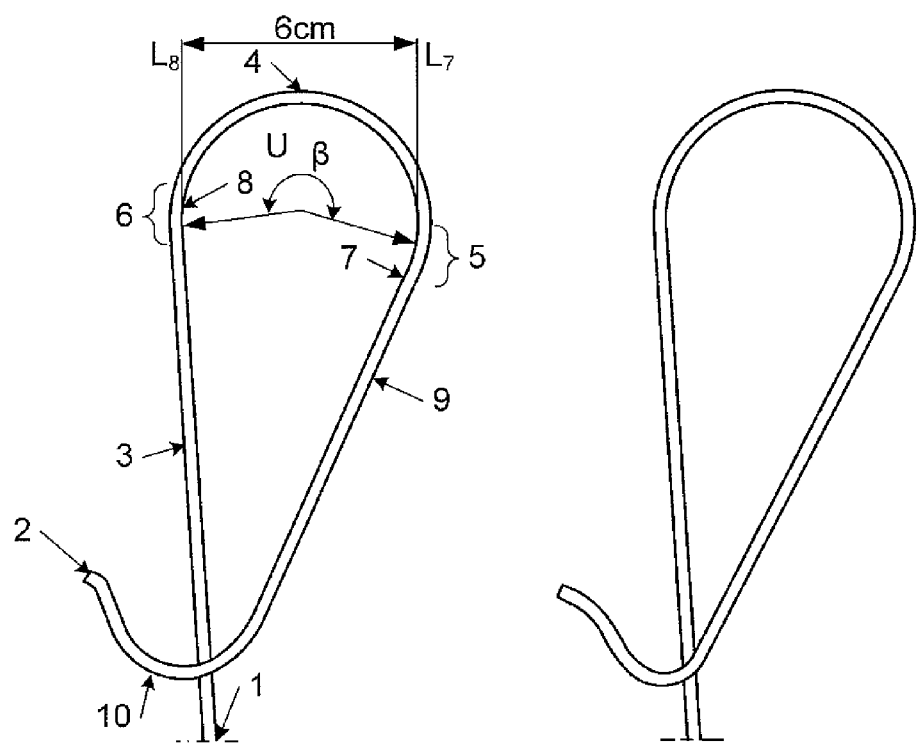
*Fig. 6a*   *Fig. 6b*
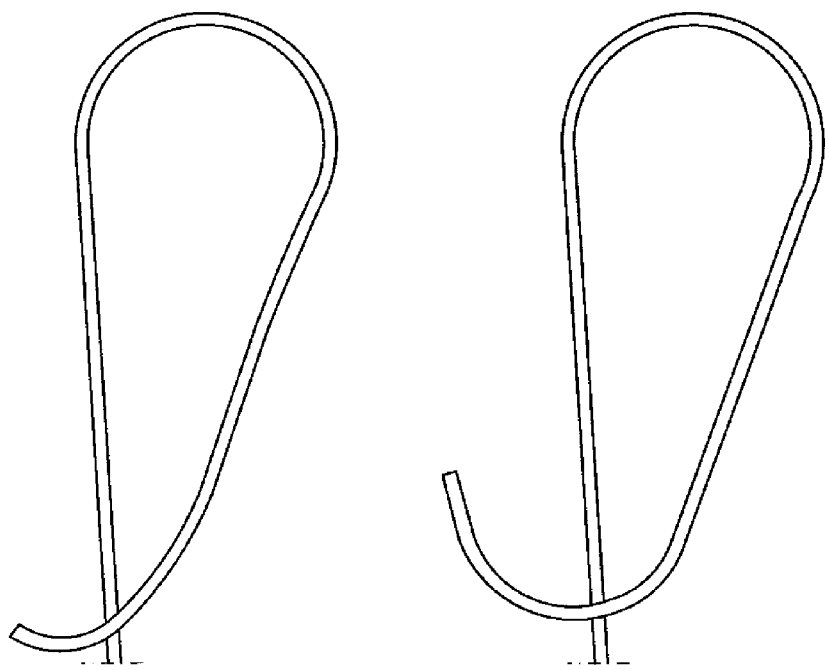
*Fig. 6c*   *Fig. 6d*

GUIDING CATHETER

The present invention relates to guiding catheter for interventional cardiology.

Percutaneous coronary intervention (PCI) is quite a recent technology aimed at relieving coronary vessel's obstruction secondary to atherosclerotic arterial wall disease. The technique of transluminal coronary angioplasty, introduced in 1977 by A. Gruntzig, consists of widening the vessel at the site of obstruction by the high hydraulic pressure applied to a fluid filled <<sausage-shaped>> balloon which is sized according to the healthy vessel's diameter. The balloon is the distal active part of a long and thin catheter-tube structure (balloon catheter).

Most of the time, after the coronary angioplasty, the enlarged lumen is thereafter (<<fixed>>) by expanding a metallic coil (<<stent>>) at the site of the angioplasty. The stent, initially <<crimped>> over a deflated balloon, is placed against the arterial wall when the balloon is inflated at very high pressure (above 10-12 atmospheres). During the following days and weeks, the healing process takes place and will cover the stent's struts, leaving an enlarged lumen at the site of the initial obstruction.

PCI is the natural evolution of the primary technique of percutaneous coronary angiography developed in the sixties by Sones, Judkins and others. The technique allows visualization of coronary artery lumen by selective injection of radio-opaque contrast material through a long pre-shaped plastic wire-braided catheter-tube. The fluid-filled angiographic (diagnostic) catheter is introduced percutaneously through a peripheral artery and is advanced in a straight form over a relatively floppy J tipped wire.

The unit <<catheter-wire>> is gently pushed in the arterial system toward the coronary artery ostium (left or right) which has to be engaged selectively. When the catheter reaches the ascending aorta, the wire is withdrawn, allowing the preformed plastic catheter to recover its preformed shape.

The catheter has to stay stable within the few first mm of the coronary vessel. The radiologic equipment allows recording of the rapid filling of the coronary artery when the radio-opaque dye is pushed within the catheter. Different pioneers designed specific shapes for such angiographic coronary catheters.

Subsequent development in plastic and catheter manufacturing (specially wire braiding process) allowed reduction of catheter's size while enlarging the effective lumen: the way was open to use these catheters, now entitled <<guiding-catheter>> as conduit for working within the coronary artery.

Required catheter's properties for selective coronary artery angiography are far different than those needed if balloon catheters and stents are to be forwarded within a coronary vessel which is small and tortuous: the principal strength of a guiding catheter will be the <<backup>> support it will provide for pushing relatively stiff materials within a more or less diseased small and often tortuous vessel.

For a given catheter size, guiding catheter <<backup>> support depends on the combination of both its shape and its body construction (type of plastic used, way of wire braiding). Of course, a larger size can improve by itself the back up support, but at the cost of a larger incision in the peripheral artery, with more risk for vascular injury and hemorrhagic events. Thus, it's important to improve the back up support through work on shape and wall manufacturing. The guiding catheter shapes are directly derived from the angiographic diagnostic catheters, the primary task being obviously to reach the coronary artery origin (the ostium). Furthermore, guiding catheter <<backup>> depends on the diameter of the catheter and on the elasticity of the catheter.

Depending on the catheter brand and type, the distal <<active>> tip of guiding catheters is shaped with a first, a secondary and sometimes a third curve: working on these different curves will give more or less <<backup>> support. The ideal guiding catheter easily engages the coronary ostium (e.g. it requires no special manipulation) and provides thereafter a strong <<backup>> support.

Each of both coronary ostia (there are two coronary arteries, the right and the left) requires a specific shaped catheter given their different localization: the right coronary artery origins below the level of the left coronary ostium and is anteriorly positioned in a frontal plane (directed toward the Sternum), the left coronary ostium being directed laterally to the left.

Historically, diagnostic coronary angiography was first performed by the transbrachial approach and required artery denudation, but it progressed rapidly to the largest and percutaneously easily accessible and straight femoral artery approach. Subsequently, PCI and dedicated diagnostic and guiding catheters adopted the same worldwide used transfemoral artery approach.

The nineties saw the development of another arterial entry site: the radial artery.

Modern interventional cardiology addresses successfully numerous different cardiac situations thanks to development of new materials and techniques.

There are three main fields in such a development:
material aimed at diagnosis and treatments of cardiac rhythm problems (<<electrophysiology>>),
material aimed at correction of anatomical structures like cardiac valves or septum defects, and
material aimed at diagnosis and treatment of coronary artery diseases.

Interventional Cardiology uses mainly percutaneous vascular accesses, either the venous system or the arterial tree for addressing different cardiac conditions. The <<tubes>> inserted in vessels are designed as <<catheters>>. When the catheter is used to introduce another piece of medical material within a cardiac structure, the term of <<guiding catheter>> is often used.

Depending of the cardiac domain (arrhythmia or electrophysiology, valves or the likes and coronary artery disease), the properties of the <<guiding catheters>> are totally different and in general, a guiding catheter designed and shaped for arrhythmia control (electrophysiology) cannot be of any help in the field of coronary artery disease.

Indeed, the diagnostic and therapeutic techniques addressing the field of cardiac rhythm problems (electrophysiology) are mainly conducted within the low pressure right heart system, through access from veins, which is a low pressure hydraulic circuit, with large and very compliant vessels easy to expand. Consequently, there is extremely low resistance when forwarding catheters in this venous system, requiring soft manipulation of catheters in order to avoid vessel damage or even rupture.

Size is not a matter for such catheters which are made of thick walls incorporating a few electric wires connected to distal electrodes. The risk of thrombosis and of severe arrhythmia due to the catheter manipulation in the venous system right heart is limited.

Most frequent venous accesses performed are the femoral, the jugular and the sub-clavicular veins. Such veins allow catheters to reach different cardiac structures and most of the time, the cardiologist has to reach and to maintain a physical contact between the catheter itself or a medical probe inserted in the lumen's catheter and the internal wall of a cardiac cavity, like the right or the left atrium, the right ventricle or the pulmonary artery.

Such large veins are also used to forward catheter-electrodes for pacemaker and defibrillator: the catheter-electrodes are anchored within the wall of the right atrium or the right ventricle or within cardiac veins.

It is very rare that such medical probe are used through the arterial tree: even intervention within the left ventricle can be performed through the venous side, thanks to the transseptal technique allowing passage of catheters from the right atrium to the left atrium and then to the left ventricle. Rarely, a trans-valvular aortic approach coming from the femoral artery is performed because this way is more arrhythmo- and thrombogenic. Furthermore, due to large size of catheter, this trans-valvular aortic approach is more prone to vascular complication because the arterial system is a high pressure circuit (10 to 15 fold the level of pressure found within the venous right heart system).

When the medical probes are properly positioned, they allow either analysis of local electrical circuit (<<mapping>>) either delivery of various destructive energy in order to modify the underlying cardiac tissue (ablation procedures).

A guiding catheter designed for electrophysiology purpose has to provide a stable position allowing a stable contact with the inner surface of a cardiac body cavity. There is no need of <<backup>> support and there is no need of small sized catheter, due to the large size and the good compliance of veins. The shape of the catheter can help for precise and easy positioning of the probe within the cardiac structure. Shape of such catheters looks eventually like shape of catheters in use in other medical or even cardiac domains, but extrapolation to these domains at least is medically hazardous.

In previous art, guiding catheters for electrophysiology studies and/or interventions have been proposed with different shapes and properties, aiming at easier probe positioning.

For example, the document U.S. Pat. No. 6,002,955 describes such a catheter for electrophysiology purpose and particularly relates to steerable electrophysiology catheters for use in mapping and ablation of cardiac tissue. Such catheters are introduced through the superior vena cava or through the inferior vena cava and their uses are strictly confined to electrophysiology.

The document EP 1920795 describes a medical apparatus related to the electrophysiology domain. Such a catheter is used for insertion into a body cavity and is inserted from left or right subclavian veins and directed to the Bachmann bundle, the septum, the pulmonary artery or the auricle. Living organs to which the medical apparatus for insertion into a body cavity is applied include the heart, the large veins, the trachea, the lung and the bladder.

More particularly, the present invention relates to a guiding catheter for coronary artery intervention through transradial access comprising a first end and a second end, and at least four main portions being:
a) a first linear portion connected to the first end,
b) a second curved portion connected to the first linear portion, said second curved portion subtending angle from 195° to 240° and presenting a distal end and a proximal end, the distance between tangential parallel lines with respect to said second curved portion passing through respectively the inner face of said distal end and the inner face of said proximal end being comprised between 5 and 7 cm, preferably about 6 cm,
c) a third linear portion, connected to the second curved portion, opposite to the first linear portion, and connected to said second end, and
d) a fourth curved portion as active distal tip provided for engaging said third linear portion (see EP 0727237).

Such a guiding catheter is for example disclosed in EP 0727237 but is unfortunately only designed for femoral access and presents a high outside diameter from about 6 to about 10 French (1 French equals ⅓ of 1 millimeter). Indeed, this document describes a <<precurved guiding introducer>> to be used for the treatment of ventricular tachycardia. This guiding introducer is introduced in the body of the left ventricle and then an ablation or mapping catheter is introduced in the lumen of the guiding catheter.

This material is strictly confined to the electrophysiology domain, mapping and/or ablation within the left ventricle from transfemoral artery access. Therefore, this material is not appropriated for coronary artery intervention through transradial access: such a guiding catheter is indeed oversized (outside diameter) for being used into the smaller brachial arterial system and does not provide a sufficient support for backup of balloon catheter to be forwarded in the coronary artery.

Another teaching is also given in the document WO 9638196 describing a guiding catheter formed from the combination of a tubular member and one or more rods insertable and movable longitudinally. The tubular member has a large central lumen to accommodate working catheters, and a shape memory. Movement of the rod along the length of the curvature imposed by the shape memory allows the user to adjust the length, shape and location of the curve in the guide catheter. Such catheter allows individualized configurations but requires more skilled operators in opposite to preformed catheters. Furthermore, the concept of moveable rod(s) within the catheter requires large catheter size and a quite straight vascular access. Unfortunately, such a catheter is not suitable for access through small and tortuous vessel like the transradial approach as used for coronary artery intervention.

The document U.S. Pat. No. 6,558,368 describes a guiding catheter for intervention in the coronary artery bed, more precisely a pre-shaped catheter having an improved distal end portion for providing more precise access to the right coronary artery, this catheter being introduced into the aorta by way of the femoral artery. Such a catheter, like the usual and classic catheters known from previous art, is designed to optimally work from the femoral artery and the shape is accordingly preformed for intervention in the right coronary artery. The shape of this catheter is more particularly designed to fit the aortic arch corning from the descending thoracic aorta.

Extrapolation from this intended use to a transradial approach, particularly from the right transradial access is at least not guaranteed, the catheter reaching the aortic arch from the right sub-clavicular artery, then the innominate artery ending in the aortic arch at the junction with the ascending aorta. Thus, coming from a right transradial access, such a pre-shaped right catheter will unfortunately direct the tip of the catheter just to the opposite side of the right coronary artery ostium. Furthermore, manipulations of the catheter to overcome this unattended opposite direction could be hazardous (risk of vascular damage), and the properties of the catheter, in term of backup support, will not be preserved.

The present invention aims to solve at least partially the aforementioned problems by providing a guiding catheter for coronary artery intervention through transradial access as described above and characterized in that said fourth curved portion is chosen in the group consisting of i) an outwardly protruding fourth curved portion presenting an opposite orientation with respect to the second curved portion and subtending an angle comprised between 185° and 245°, preferably between 190° and 240°, more preferably about 225°, ii) an inwardly protruding fourth curved portion subtending an angle comprised between 75° and 115°, preferably between 85° and 95°, more preferably about 90° and overlapping, in a planar view said first linear portion, and in that the outside diameter of said guiding catheter is less than 6 French.

The fact that the outside diameter of the guiding catheter according to the present invention is less than 6 French allows coronary artery intervention through transradial access, this diameter being adapted to an access through the sinuous, spasm-prone and more thrombogenic arterial tree of the upper extremities. Preferably, the outside diameter is less than 5 French. This diameter, combined with the first, second, third and fourth portions of the guiding catheter further provides backup support with a guiding catheter having a common design for left or right coronary artery or left or right transradial artery to which only the distal tip will change, thereby rendering manufacturing very easy (only a few models have to be constructed).

Furthermore, the fact that said fourth curved portion is an outwardly protruding curved portion subtending an angle comprised between 185° and 245° or is an inwardly protruding curved portion subtending an angle comprised between 75° and 115° ensures a correct backup of the guiding catheter, these specific angles providing a backup support even if the outside diameter of the guiding catheter is less than 6 French. On one hand, these angles define a predetermined curve of said fourth portion and therefore help introducing the catheter into the ostium. On the other end, these angles provide a support for a correct backup of the guiding catheter.

For intervention in the left coronary artery through right transradial artery, the fourth curved portion presents an opposite orientation with respect to the second curved portion and subtends an angle α comprised between 185° and 245°, preferably between 190° and 240°, more preferably about 225°.

For intervention in the right coronary artery through right transradial artery, said fourth curved portion overlaps, in a planar view said first linear portion and subtends an angle α comprised between 75° and 115°, preferably between 85° and 95°, more preferably about 90°.

Despite being technically more challenging, the transradial approach is gaining more and more acceptance due to a better clinical safety profile: vascular complications and secondary hemorrhagic events are far less frequent and more easily managed. The difficulties of this access are related firstly to the puncture of the radial artery itself (the vessel's size is small) and secondly to the arterial tree connecting the radial artery to the coronary ostia. The way catheters must follow when performing catheterization from the wrist to the heart is obviously far different than the way used starting from the femoral artery: the radial artery itself is of small size (thus limiting the usable size of catheter), is prone to spasm (leading to difficult manipulations) and is often associated with loops or tortuosities (as often seen at the junction between the radial and the brachial artery, at the elbow level).

The brachial artery is larger and is usually easy to cross and connect to the axillary and then the right sub-clavicular artery, forming a normally gentle bend followed by the brachiocephalic (innominate) artery: this artery enters the aorta at its transversal arch. This last junction, before the ascending aorta is a level of frequent problems, due to tortuosities and bending, often secondary to atherosclerotic disease and aging.

The transradial approach triggered the development of new shapes for coronary diagnostic and guiding catheters, as true as existing catheters were designed for a femoral access and are not ideally suited for a transradial catheterization, particularly starting from the right radial artery.

By contrast, the left transradial approach, requiring the same skill for puncturing the vessel and manipulating catheter along the left arm, avoids the problem of the brachiocephalic (innominate) artery. The left subclavian artery connect directly to the aortic arch and the aging or the atherosclerotic disease does not perturb the anatomy as much as for the innominate artery on the right side: except for the uncomfortable position of the operator working with the patient's left arm, this arterial way is usually easier and much like the femoral way in term of ease of catheter manipulation. Catheters designed for the femoral approach <<work>> as well from this left radial access. It is important to understand that catheter's performances are truly dependent of the arterial approach used and that guiding catheters should be classified according both to the approach and to the specific coronary artery for which they were designed initially.

Up to now, availability is limited regarding small sized (5 and 6F) guiding catheters well suited for the right radial artery approach conferring appropriate backup support during the further steps of manipulation within the coronary artery and which stays perfectly in place during the removal or introduction of further material. The radial environment is indeed prone to spasm (best avoided with small sized catheters) while the coronary tree is also of small diameter and highly tortuous. This can lead to guiding catheter displacement between the time when the material is inserted or removed and next step of work is performed or between the time when visualisation through contrast liquid is done and work is performed. There is therefore a strong need to provide small sized guiding catheter with a high backup support.

The fact that the second curved portion subtends an angle from 195° to 240° allows a <<pendulum>> or balance movement of the active distal tip which stays well aligned within the coronary lumen thanks to the floppy coronary guide wire always introduced in the coronary artery as the first step of any coronary intervention.

Thus, the present invention can represent a new platform or family of guiding catheters, giving the benefit of a constant backup support, platform related, and the flexibility of different distal tips meeting operator's expectation or some specific anatomic need. The new curve is especially designed for the right radial access to the coronary artery, even if the curve may apply for left radial access.

The centre of the pendulum points at the second curved portion and is usually located at the catheter's entry in the ascending aorta for the right transradial access. With this added second curved portion, the catheter, once selectively engaged in the ostium of a coronary artery, is <<forced>> to come back in the ostium when a backward force is applied (which is happening each time a coronary interventional material is forwarded through the coronary vessel). Moreover, the coronary guide wire (always present) helps the tip of the guiding catheter to stay well aligned and coaxial in the coronary ostium thus minimizing the possible damage to the vessel wall or the ostium itself. Because of the tortuous environment, the operator must apply a pushing effect to a material inserted through the proximal end of the guiding catheter, and it is need that the effort is transmitted to the distal end of this material while it advances through the coronary vessel. Such force applies also to the guiding catheter, but in an opposite direction. The second curved portion subtending an angle from 195° to 240° confers a hook shape particularly adapted to the anatomy of the vessels reaching the aortic arch, the curved portion providing support, i.e. allows to compensate for this backward force applied to the guiding catheter and allows to revert to the initial shape by the pendulum effect. Furthermore, specific manufactory processes applied to the wall of the guiding catheter at the level of this second curved portion may reinforce both the backward support and the ability to revert to the initial shape.

Advantageously, said second curved portion subtends an angle β from 200° to 220°, preferably about 210°.

According to the invention, the guiding catheter comprises a fourth curved portion as fourth portion between the third linear portion and said second end, said fourth portion being a variety of active distal tip(s). These active distal tips may be chosen, for example, from classic and usual curves known from previous art, like all the family of Judkins (left and right), Amplatz (left and right), . . .

The usual and classic active tips as known from previous art allow coronary artery's ostium precise engagement without requiring from operator to change their technique.

According to an embodiment of the present invention, the second curved portion comprises a top or maximum and wherein the fourth portion, preferably the fourth curved portion comprises a base or minimum, the distance L between parallel horizontal line passing through respectively the inner face of the maximum (or top) of said second curved portion and the inner face of the minimum (or base) of the fourth portion is comprised between 11 and 14 cm, preferably between 11.5 and 12.5 cm, more preferably between 12 and 13 cm.

The top of the second curved portion is placed at about 13 cm from the base of the distal active tip (13 cm from the inner edge of the second curved portion to the base inner edge of the fourth portion being the active distal part) to provide not only a good support but also a more stable position of the catheter within the artery.

In a variant of the further embodiment of the guiding catheter according to the invention, the second curved portion comprises a maximum or top and wherein the fourth portion, preferably the fourth curved portion comprises a minimum or base, the distance between parallel horizontal line passing through respectively the inner face of the maximum or top of said second curved portion and the inner face of the minimum or base of the fourth portion is comprised between 6.5 and 9.5 cm, preferably between 7 and 9 cm, more preferably about 8 cm.

Preferably, said outwardly protruding fourth curved portion present a distal end and a proximal end, the distance between parallel lines passing through respectively the inner face of said distal end and the inner face of said proximal end being comprised between 3 to 5 cm, preferably between 3.5 and 4.5 cm, more preferably about 4 cm, for a better relationship between the coronary artery and the guiding catheter, thereby providing more stability and reduced stress constraint on said artery.

The active distal portion of this guiding catheter renders the guiding catheter according to the invention designed as a right transradial approach for a left coronary artery guiding catheter, the second curved portion is prolonged by a specific active curved distal tip (A) giving a global <<S>> shape.

Preferably, said fourth curved portion i) comprises a minimum or base, the distance between the horizontal line passing through said minimum or base and the parallel horizontal line passing through said second end is comprised between 2 and 4 cm, preferably between 2.5 and 3.5 and more preferably about 3 cm.

Further, in a preferred embodiment, the active distal tip being the inwardly protruding fourth curved portion ii) comprises a minimum or base, the distance between the horizontal line passing through said minimum or base and the parallel horizontal line passing through said second end is comprised between 0.5 and 2 cm, preferably about 1 cm.

This design of the active distal tip of the guiding catheter according to the invention allows a more close relationship between the coronary artery and the guiding catheter, thereby providing more stability and reduced stress constraint on said artery.

Advantageously, in another variant according to the invention, said second end is inscribed in another plane with respect to the main plane wherein the catheter is inscribed, giving to the catheter a three dimensional configuration. The active curved distal tip may be located for 10 to 30° more anteriorly or more posteriorly.

The same guiding catheter according to the present invention, especially according to the present variant with a second curved portion allowing a pendulum effect can also be used for the left transradial approach for a left coronary artery guiding catheter provided that the fourth curved portion is shaped to fit the position of the left coronary ostium. In this situation, the centre of the pendulum (maximum of the second curved portion) is located in the left subclavian artery, when the artery bends toward the aortic arch.

Other embodiments of the guiding catheter according to the invention are mentioned in the annexed claims.

Other characteristics and advantages of the invention will appear more clearly in the light of the following description of a particular non-limiting embodiment of the invention, while referring to the figures.

FIGS. 6a to 6g illustrate different forms of the guiding catheter according to the invention designed as a catheter for right transradial approach and for PCI of a right coronary artery (RCA).

FIG. 1 illustrates the three main ways to access for introducing catheter: through the right radial artery (A), through the left radial artery (B) and through the femoral artery (C).

Figure 1:
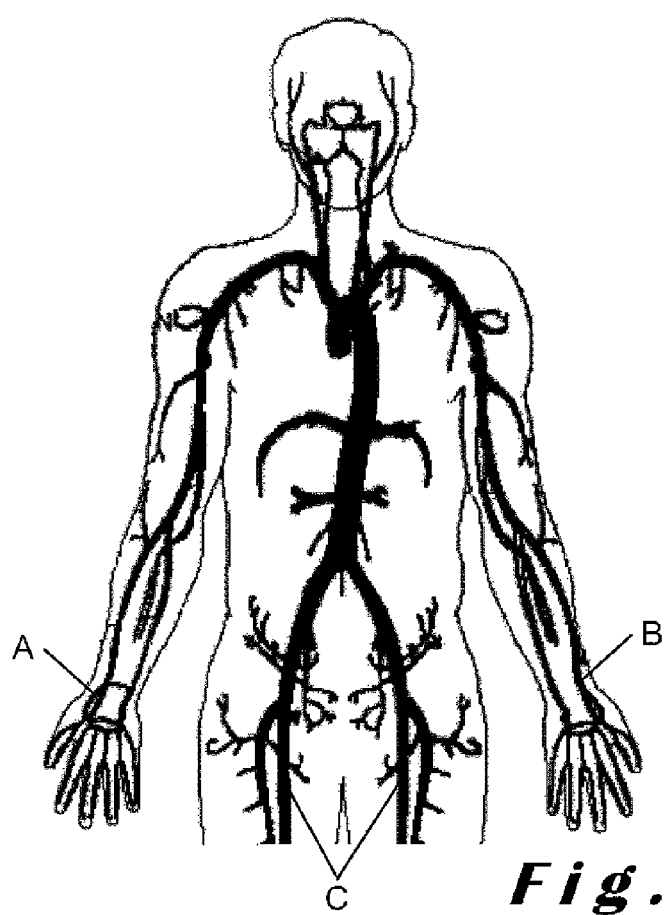
FIGS. 1 and 2 are views of the human main arterial system, illustrating the different way a catheter has to go through for coronary artery cannulation depending of the site of the vascular access.
Figure 2:
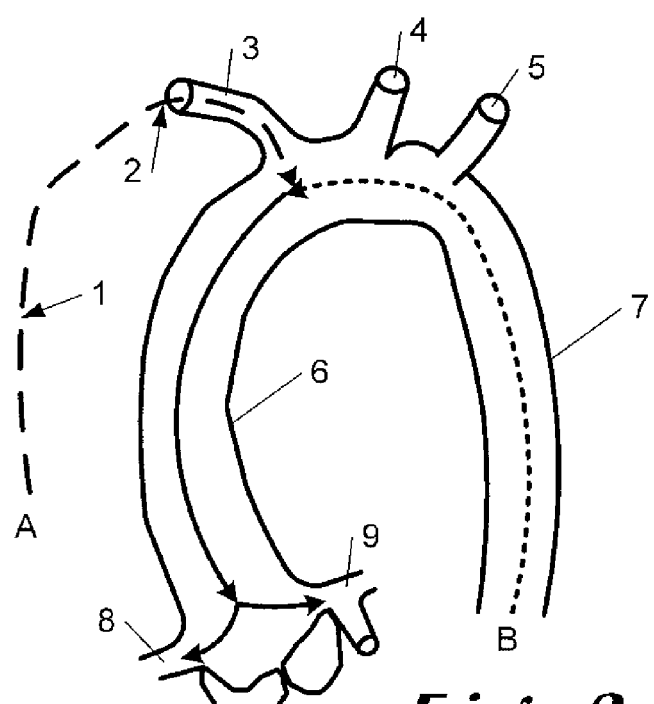

FIG. 2 illustrates accesses through a radial artery (A) or through the femoral artery (B) and shows the different arteries and aortas involved when introducing a catheter. Brachial artery (1), subclavicular artery (2), innominate artery (3), left carotid artery (4), left subclavian artery (5), thoracic ascending aorta (6), thoracic descending aorta (7), right coronary artery (8) and left coronary artery (9).

Figure 3:
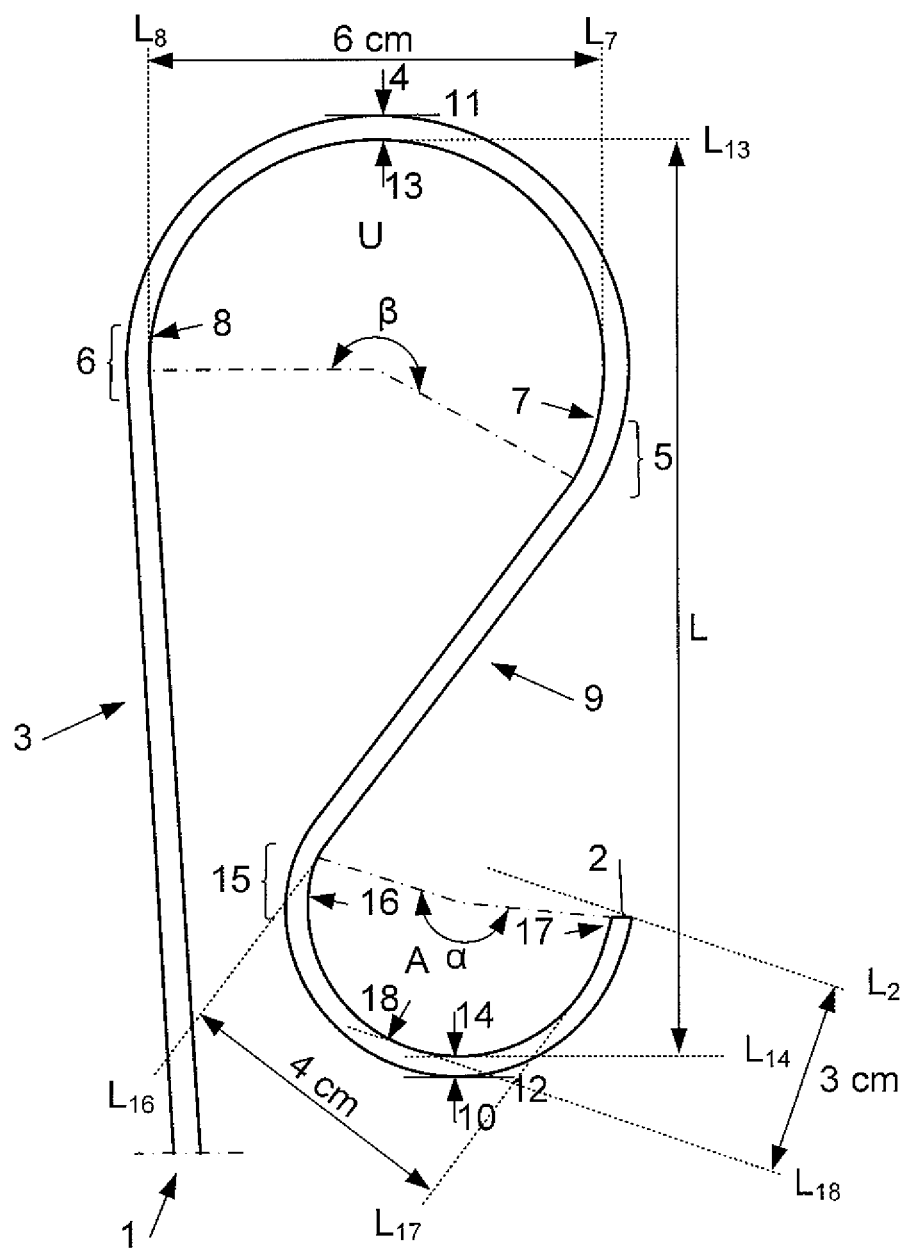
FIG. 3 illustrates the guiding catheter according to the invention designed as a catheter for right transradial approach and for percutaneous coronary intervention (PCI) of a left coronary artery (LCA), the distal active tip being a special embodiment.

FIG. 3 illustrates the guiding catheter according to the invention designed as a catheter for right transradial approach and for percutaneous coronary intervention (PCI) of a left coronary artery (LCA).

This catheter comprises a first end 1 (proximal end) and a second end 2 (distal end), and a first linear portion 3 connected to the first end 1. A second curved portion 4 is further connected to the first linear portion 3 and a third linear portion 9 is connected to the second curved portion 4, opposite to the first linear portion 3, and connected to said second end 2.

The second curved portion 4 subtends an angle β from 195° to 240°, preferably from 200° to 220°, preferably about 210°. The third linear portion 9 is provided to engage with an active distal tip 10 (of variable shape), as fourth portion 10 terminating at said second end 2.

The second curved portion 4 presents a proximal end 6 and a distal end 5. The distance between parallel lines passing through respectively the inner face 7 of said distal end 5 (L7) and the inner face 8 of said proximal end 6 (L8) being comprised between 5 and 7 cm, preferably about 6 cm.

The second curved portion 4 comprises a maximum 11. The fourth portion 10, preferably the fourth curved portion 10 comprises a minimum 12. The distance L between parallel horizontal lines passing through respectively the inner face 13 of the maximum 11 of said second curved portion (L13) and the inner face 14 of the minimum 12 of the fourth curved portion 10 (L14) is comprised between 11 and 14 cm, preferably between 11.5 and 13.5 cm, more preferably between 12 and 13 cm.

The said fourth curved portion 10 presents an opposite orientation with respect to the second curved portion 4 and subtends an angle comprised between 185° and 245°, preferably between 190° and 240°, more preferably about 225°.

The fourth curved portion presents a distal end 15, the distance between parallel lines passing through respectively the inner face 16 of said distal end 15 (L16) and the inner face 17 of said tip or end 2 (L17) being comprised between 3 to 5 cm, preferably between 3.5 and 4.5 cm, more preferably about 4 cm.

The fourth curved portion 10 comprises a mid to distal end 18, the distance between the horizontal line passing through said mid to distal end 18 (L18) and the parallel horizontal line passing through said tip or second end 2 (L2) is comprised between 2 and 4 cm, preferably between 2.5 and 3.5 and more preferably about 3 cm.

Therefore, the U shaped curved portion 4 is prolonged by a specific active curved end 10 giving a global <<S>> shape. This curved end has preferably a length of 4 cm, following a 225±5° circle's arc, the radius of the circle being of 2 cm, the tip 10 is located at 2.75 to 3.25 cm from the inner edge of the active distal curve. This added pre shaped active distal tip 10 is directed in the opposite direction regarding the second curved portion 4.

The U curved portion 4 stays at a distance of 13 cm from the inner edge of the curved U portion 4 to the inner edge of the active pre shaped end 10 of the guiding catheter.

In a variant the said distance L is comprised between 6.5 and 9.5 cm, preferably between 7 and 9 cm, more preferably about 8 cm.

The second curved portion 4 therefore describes a large U shaped curve (U) of about 6 cm in diameter for a circle's arc of about at least 210° and is located at about 13 cm (L) from the inner edge of the curved U portion to the inner edge of the pre shaped active end also called distal tip 10 of the guiding catheter. This U shaped curve may be located more proximally (L<13 cm) for catheters designed for special purposes like patient with a low body status or for PCI of saphenous vein graft (SVG): the origin of a SVG is always lying in a upper position within the ascending aorta.

The U shaped curve may also be located more distally (L>13 cm) for severely enlarged ascending aorta, coronary ostia being more deeply positioned.

Active distal tip 10 of any actually known coronary catheter curve for coronary artery PCI, (e.g. Judkins, Amplatz, etc. . . . ) may be used provided that their shape don't already comprise a fourth curve as for the Arani or the Muta or the Ikari catheter and the likes. For a right transradial approach and for a guiding catheter designed for intervention within the left coronary artery, the added pre-shaped active end 10 is directed in the opposite direction regarding the second curved portion that is U shaped 4.

As will be discussed later, for the same right transradial approach, but for a guiding catheter designed for the right coronary artery, the added pre shaped active end 10 is directed toward the second curved U shaped portion 4, in such a way that the added active end 10 closes the loop initiated by the U turn curve 4.

Figures 4A, 4B, 4C:
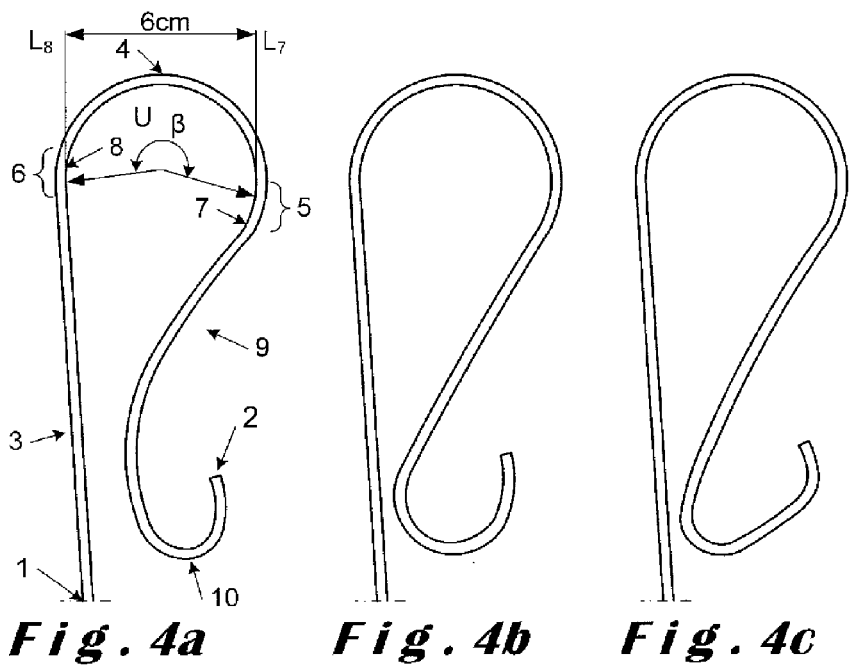
FIGS. 4a to 4f illustrate different forms of the guiding catheter according to the invention designed as a catheter for right transradial approach and for percutaneous coronary intervention (PCI) of a left coronary artery (LCA) catheter.
Figures 4D, 4E, 4F:
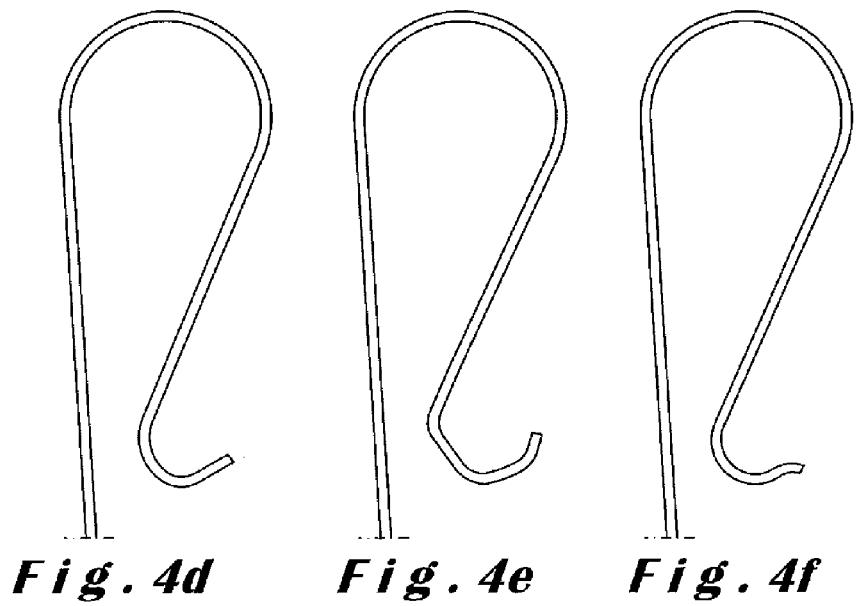

FIG. 4a illustrates the guiding catheter according to the invention with a distal tip EBU, FIG. 4b illustrates the guiding catheter according to the invention with a distal tip JCL, FIG. 4c illustrates the guiding catheter according to the invention with a distal tip JL, FIG. 4d illustrates the guiding catheter according to the invention with a distal tip MAC, FIG. 4e illustrates the guiding catheter according to the invention with a distal tip MRadial and FIG. 4f illustrates the guiding catheter according to the invention with a distal tip AL.

Figure 5:
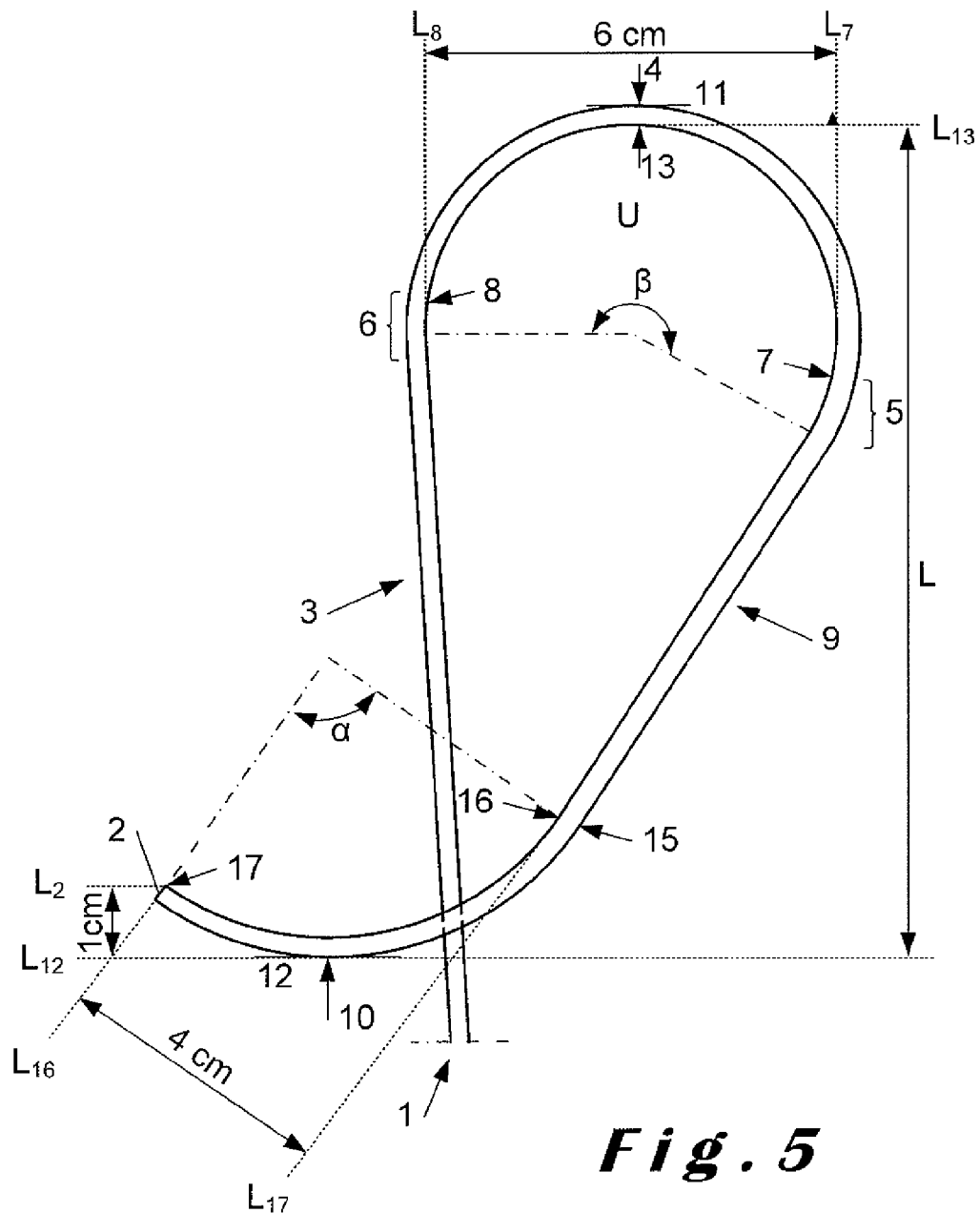
FIG. 5 illustrates the guiding catheter according to the invention designed as a catheter for right transradial approach and for PCI of a right coronary artery catheter, the distal active tip being a special embodiment.

The FIG. 5 illustrates guiding catheter according to the invention designed as catheter for a right transradial access and for right coronary artery PCI. The fourth curved portion 10 presents an orientation toward the second curved portion 4, overlaps in a planar view said first linear portion 3 and subtends an angle comprised between 75° and 115°, preferably between 85° and 95°, more preferably about 90°.

The fourth curved portion 10 presents a proximal end 15 and a distal end 2, the distance between parallel lines passing through respectively the inner face 16 of said proximal end 15 (L17) and the inner face 17 of said distal end 2 (L16) being comprised between 3 to 5 cm, preferably about 3.5 and 4.5 cm, more preferably about 4 cm.

The fourth curved portion 10 further comprises a minimum 12, the distance between the horizontal line passing through said minimum (L12) and the parallel horizontal line L2 passing through said second end 2 is comprised between 0.5 and 2 cm, preferably about 1 cm.

Accordingly, the distal active tip 10 has a curved portion of about 4 cm in length, following a 90±5° circle's arc, the radius of the circle being of about 3±0.2 cm ending in a gentle upper bend; the tip 10 is at 1 to 2 cm from the inner edge of the distal curve. The U curved portion 4 stays at a distance of 13 cm from the inner edge of the curved U portion 4 to the inner edge of the active pre shaped end 10 of the guiding catheter.

Figure 6G:
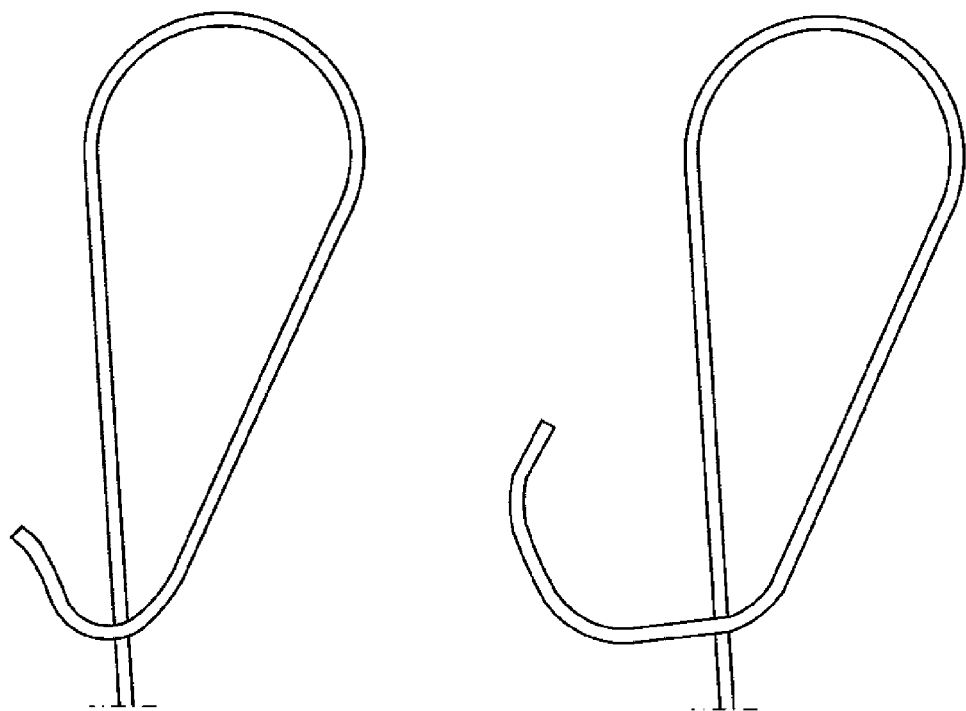
Figure 6G:
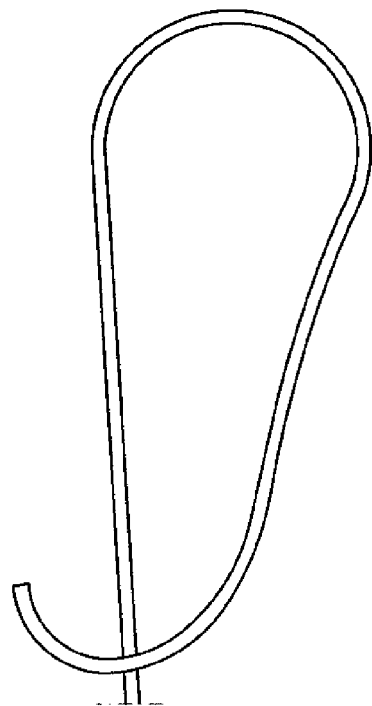

FIG. 6a illustrates the guiding catheter according to the invention with a distal tip Amplatz, FIG. 6b illustrates the guiding catheter according to the invention with a distal tip Amplatz right, FIG. 6c illustrates the guiding catheter according to the invention with a distal tip Judkins, FIG. 6d illustrates the guiding catheter according to the invention with a distal tip MAC, FIG. 6e illustrates the guiding catheter according to the invention with a distal tip SAL, FIG. 6f illustrates the guiding catheter according to the invention with a distal tip MRadial, FIG. 6g illustrates the guiding catheter according to the invention with a distal tip SCR.

Although the preferred embodiments of the invention have been disclosed for illustrative purpose, those skilled in the art will appreciate that various modifications, additions or substitutions are possible, without departing from the scope and spirit of the invention as disclosed in the accompanying claims.

For example, the Guiding catheter according to the invention is also provided with a distance between parallel horizontal line passing through respectively the inner face of the maximum of said second curved portion and the inner face of the minimum of the fourth curved portion which is reduced to less than 13 cm aimed for PCI of diseased saphenous vein graft through the right trans radial approach.

In other variant according to the invention, the guiding catheter according to the invention is also provided with a distance between parallel horizontal line passing through respectively the inner face of the maximum of said second curved portion and the inner face of the minimum of the fourth curved portion which is increased to more than 13 cm aimed for PCI through the right trans radial approach when the ascending aorta is severely enlarged.

The invention claimed is:

1. A guiding catheter for coronary artery intervention in a left coronary artery or a right coronary artery through right transradial access comprising a first end and a second end, and at least four main portions comprising:
   a) a first linear portion connected to the first end,
   b) a second curved portion connected to the first linear portion, said second curved portion subtending an angle β from 195° to 240° and presenting a distal end and a proximal end, a distance between tangential parallel lines with respect to said second curved portion passing through respectively an inner face of said distal end and an inner face of said proximal end being between 5 and 7 cm,
   c) a third linear portion, connected to the second curved portion, opposite to the first linear portion, and connected to said second end,
   d) a fourth curved portion as an active distal tip provided for engaging said third linear portion,
   wherein said fourth curved portion is chosen from a group consisting of
   i) an outwardly protruding fourth curved portion presenting an opposite orientation with respect to the second curved portion and subtending an angle α between 185° and 245°, for intervention in the left coronary artery, in which the angle α is measured between a proximal end of the outwardly protruding fourth curved portion and a distal end of the outwardly protruding fourth curved portion, and
   ii) an inwardly protruding fourth curved portion subtending an angle α from 75° and 115°, for intervention in the right coronary artery, a proximal end of the inwardly protruding fourth curved portion being on a first side of the first linear portion and a distal end of the inwardly protruding fourth curved portion being on a second side of the first linear portion opposite the first side,
   and wherein an outside diameter of said guiding catheter is less than 6 French.

2. The guiding catheter according to claim 1, wherein said second curved portion subtends the angle β of 200° to 220°.

3. The guiding catheter according to claim 2, wherein said second curved portion subtends the angle β at 210°.

4. The guiding catheter according to claim 1, wherein the second curved portion comprises a maximum or top and wherein the fourth curved portion comprises a minimum or base, a distance between parallel horizontal lines passing through respectively an inner face of the maximum or top of said second curved portion and an inner face of the minimum or base of the fourth portion being between 11 and 14 cm.

5. The guiding catheter according to claim 4, wherein the distance between parallel horizontal lines passing through the inner face of the maximum or top of said second curved portion and the inner face of the minimum or base of the fourth portion is between 12 and 13 cm.

6. The guiding catheter according to claim 1, wherein the second curved portion comprises a maximum or top and wherein the fourth curved portion comprises a minimum or base, a distance between parallel horizontal line passing through respectively an inner face of the maximum or top of said second curved portion and an inner face of the minimum or base of the fourth portion being between 6.5 and 9.5 cm.

7. The guiding catheter according to claim 6, wherein the distance between parallel horizontal lines passing through the inner face of the maximum or top of said second curved portion and the inner face of the minimum or base of the fourth portion is 8 cm.

8. The guiding catheter according to claim 1, wherein a distance between tangential parallel lines with respect to said fourth curved portion passing through respectively an inner face of said fourth curved portion distal end and an inner face of said fourth curved portion proximal end being between 3 and 5 cm.

9. The guiding catheter according to claim 8, wherein the distance between tangential parallel lines with respect to said fourth curved portion passing through the inner face of said fourth curved portion distal end and the inner face of said fourth curved portion proximal end is 4 cm.

10. The guiding catheter according to claim 1, wherein the outwardly protruding fourth curved portion i) comprises a minimum or base, a distance between a horizontal line passing through said minimum or base and a parallel horizontal line passing through said second end being between 2 and 4 cm.

11. The guiding catheter according to claim 10, wherein the distance between the horizontal line passing through the minimum or base of the outwardly protruding fourth curved portion and the parallel horizontal line passing through said second end is 3 cm.

12. The guiding catheter according to claim 1, wherein said inwardly protruding fourth curved portion ii) further comprises a minimum or base, a distance between a horizontal line passing through said minimum or base and a parallel horizontal line passing through said second end being between 0.5 and 2 cm.

13. The guiding catheter according to claim 12, wherein the distance between the horizontal line passing through said minimum or base of the inwardly protruding fourth curved portion and the parallel horizontal line passing through said second end is 1 cm.

14. The guiding catheter according to claim 1, wherein said second end is inscribed in another plane more anteriorly or more posteriorly with respect to a main plane wherein the catheter is inscribed.

15. The guiding catheter according to claim 1, wherein the angle $\alpha$ in the outwardly protruding fourth curved portion is between 190° and 240°.

16. The guiding catheter according to claim 1, wherein the angle $\alpha$ in the outwardly protruding fourth curved portion is 225°.

17. The guiding catheter according to claim 1, wherein said angle $\alpha$ in the inwardly protruding fourth curved portion between 75° and 115° is between 85° and 95°.

18. The guiding catheter according to claim 1, wherein said angle $\alpha$ in the inwardly protruding fourth curved portion between 75° and 115° is 90°.

19. The guiding catheter according to claim 1, wherein the distance between tangential parallel lines with respect to the second curved portion passing through the inner face of the distal end and the inner face of the proximal end is 6 cm.

* * * * *